(12) United States Patent
Kudis et al.

(10) Patent No.: US 6,613,719 B1
(45) Date of Patent: Sep. 2, 2003

(54) 3-(4,5-DIHYDROISOXAZOL-3-YL)-SUBSTITUTED BENZOYLPYRAZOLES

(75) Inventors: Steffen Kudis, Mannheim (DE); Ernst Baumann, Dudenhofen (DE); Wolfgang von Deyn, Neustadt (DE); Klaus Langemann, Worms (DE); Guido Mayer, Neustadt (DE); Ulf Misslitz, Neustadt (DE); Ulf Neidlein, Mannheim (DE); Matthias Witschel, Bad Dürkheim (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,848

(22) PCT Filed: Nov. 27, 2000

(86) PCT No.: PCT/EP00/11820

§ 371 (c)(1),
(2), (4) Date: May 23, 2002

(87) PCT Pub. No.: WO01/40220

PCT Pub. Date: Jun. 7, 2001

(30) Foreign Application Priority Data

Dec. 2, 1999 (DE) .......................................... 199 58 032

(51) Int. Cl.$^7$ .................. A01N 43/80; C07D 413/10
(52) U.S. Cl. ........................................ 504/271; 548/240
(58) Field of Search ........................... 548/240; 504/271

(56) References Cited

U.S. PATENT DOCUMENTS 6,165,944 A  * 12/2000 von Deyn et al. .......... 504/271
6,506,708 B1 *  1/2003 Neidlein et al. ............ 548/240

* cited by examiner

Primary Examiner—Robert W. Ramsuer
(74) Attorney, Agent, or Firm—Keil & Weinkauf

(57) ABSTRACT

3-(4,5-Dihydroisoxazol-3-yl)-substituted benzoylpyrazoles of the formula I

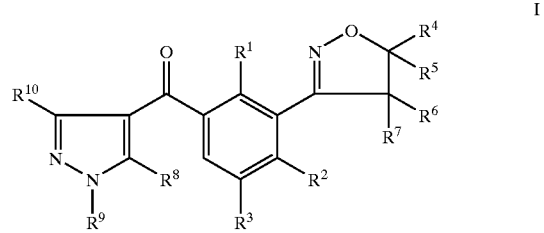

in which $R^4$ is $C_1$–$C_4$-haloalkyl and $R^1$ to $R^3$ and $R^5$ to $R^{10}$ are as defined in the description are described. The compounds have herbicidal activity.

10 Claims, No Drawings

3-(4,5-DIHYDROISOXAZOL-3-YL)-SUBSTITUTED BENZOYLPYRAZOLES

The present invention relates to certain 3-(4,5-dihydroisoxazol-3-yl)-substituted benzoylpyrazoles and to processes for their preparation, to compositions comprising them and to the use of these derivatives or of the compositions comprising them for controlling harmful plants.

The literature, for example WO 96/26206, WO 98/31682 and WO 98/31681, discloses pyrazol-4-yl-benzoyl derivatives.

The earlier applications WO 00/34273, WO 00/34272, DE 19936520.2 and DE 19936518.0 describe, inter alia, (4,5-dihydroisoxazol-3-yl)-substituted benzoylpyrazoles and their herbicidal properties. They do not describe the compounds of the formula I defined below.

However, the herbicidal properties of the prior-art compounds and their compatibility with crop plants are not entirely satisfactory. It is an object of the present invention to provide novel, in particular herbicidally active, compounds having improved properties.

We have found that this object is achieved by the 3-(4,5-dihydroisoxazol-3-yl)-substituted benzoylpyrazoles of the formula I

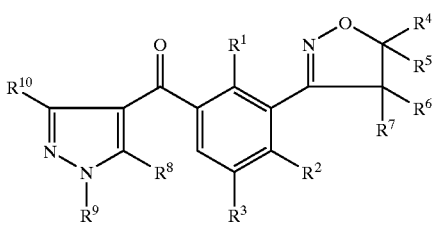

in which
R$^1$ is C$_1$–C$_6$-alkyl, C$_1$–C$_6$-haloalkyl, C$_1$–C$_6$-alkoxy or C$_1$–C$_6$-haloalkoxy;
R$^2$ is C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl or C$_1$–C$_6$-haloalkylsulfonyl, halogen, cyano or nitro;
R$^3$ is hydrogen, C$_1$–C$_6$-alkyl or halogen;
R$^4$ is C$_1$–C$_4$-haloalkyl;
R$^5$, R$^6$, R$^7$ independently of one another are hydrogen, C$_1$–C$_4$-alkyl or C$_1$–C$_4$-haloalkyl;
R$^8$ is hydroxyl, C$_1$–C$_6$-alkoxy, C$_3$–C$_6$-alkenyloxy, C$_1$–C$_6$-alkylsulfonyloxy, C$_1$–C$_6$-alkylcarbonyloxy, phenyl-C$_1$–C$_4$-alkoxy, phenylcarbonyl-C$_1$–C$_4$-alkoxy, phenylsulfonyloxy or phenylcarbonyloxy, where the phenyl radical of the four lastmentioned substituents may be partially or fully halogenated and/or may carry one to three of the following groups: nitro, cyano, C$_1$–C$_4$-alkyl, C$_1$–C$_4$-haloalkyl, C$_1$–C$_4$-alkoxy or C$_1$–C$_4$-haloalkoxy;
R$^9$ is hydrogen or C$_1$–C$_2$-alkyl; and
R$^{10}$ is hydrogen or C$_1$–C$_4$-alkyl;
and their agriculturally useful salts.

Furthermore, we have found herbicidal compositions which comprise the compounds I and have very good herbicidal action. Moreover, we have found processes for preparing these compositions and methods for controlling undesirable vegetation using the compounds I.

Depending on the substitution pattern, the compounds of the formula I can contain one or more chiral centers, in which case they are present as enantiomer or diastereomer mixtures. The invention provides both the pure enantiomers or diastereomers and their mixtures.

Compounds of the formula I may also be present in the form of their agriculturally useful salts, the nature of the salt generally being immaterial. In general, the salts of those cations or the acid addition salts of those acids are suitable whose cations and anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogens may be replaced by C$_1$–C$_4$-alkyl, hydroxy-C$_1$–C$_4$-alkyl, C$_1$–C$_4$-alkoxy-C$_1$–C$_4$-alkyl, hydroxy-C$_1$–C$_4$-alkoxy-C$_1$–C$_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri(C$_1$–C$_4$-alkyl)sulfonium and sulfoxonium ions, preferably tri(C$_1$–C$_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of C$_1$–C$_4$-alkanoic acids, preferably formate, acetate, propionate and butyrate.

The organic moieties mentioned for the substituents R$^1$–R$^{10}$ or as radicals on phenyl rings are collective terms for individual enumerations of the individual group members. All hydrocarbon chains, i.e. all alkyl, alkylcarbonyl, haloalkyl, alkoxy, haloalkoxy, alkylcarbonyloxy, alkylsulfonyloxy, alkylthio, alkylsulfinyl, haloalkylsulfinyl, haloalkylthio, alkylsulfonyl, haloalkylsulfonyl, alkenyl, alkenyloxy, phenylalkyl, phenylcarbonylalkyl, phenylalkoxy and phenylcarbonylalkoxy moieties can be straight-chain or branched. Unless indicated otherwise, halogenated substituents preferably carry one to five identical or different halogen atoms. The term halogen denotes in each case fluorine, chlorine, bromine or iodine.

Examples of other meanings are:

C$_1$–C$_2$-alkyl, and the alkyl moieties of phenyl-C$_1$–C$_2$-alkyl and phenylcarbonyl-C$_1$–C$_2$-alkyl: methyl or ethyl;

C$_1$–C$_4$-alkyl, and the alkyl moieties of C$_1$–C$_4$-alkylcarbonyl, C$_1$–C$_4$-alkylcarbonyloxy, phenyl-C$_1$–C$_4$-alkyl and phenylcarbonyl-C$_1$–C$_4$-alkyl: C$_1$–C$_2$-alkyl as mentioned above, and also propyl, 1-methylethyl, butyl, 1-methylpropyl, 2-methylpropyl and 1,1-dimethylethyl;

C$_1$–C$_6$-alkyl, and the alkyl moieties of C$_1$–C$_6$-alkylcarbonyl and C$_1$–C$_6$-alkylcarbonyloxy: C$_1$–C$_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

C$_1$–C$_2$-haloalkyl: a C$_1$–C$_2$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, bromomethyl, iodomethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-haloalkyl: $C_1$–$C_2$-haloalkyl as mentioned above, and also, for example, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_2$-alkoxy as alkoxy moieties of phenyl-$C_1$–$C_2$-alkoxy and phenylcarbonyl-$C_1$–$C_2$-alkoxy: methoxy or ethoxy;

$C_1$–$C_4$-alkoxy, and the alkoxy radicals of phenyl-$C_1$–$C_4$-alkoxy and phenylcarbonyl-$C_1$–$C_4$-alkoxy: $C_1$–$C_2$-alkoxy as mentioned above, and also, for example, propoxy, 1-methylethoxy, butoxy, 1-methylpropoxy, 2-methylpropoxy and 1,1-dimethylethoxy;

$C_1$–$C_6$-alkoxy: $C_1$–$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_6$-alkylthio: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, 25 and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S($=$O)$_2$—), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl, and the alkylsulfonyl moieties of $C_1$–$C_6$-alkylsulfonyloxy: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-bromohexylsulfonyl, 6-iodohexylsulfonyl or dodecafluorohexylsulfonyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex- 1-en-1-yl, hex-2-en-1-yl, hex-3-en-1-yl, hex-4-en-1-yl, Hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

The phenyl rings of the radicals phenylalkyl, phenylcarbonylalkyl, phenylalkoxy, phenylcarbonylalkoxy, phenylsulfonyl, phenylsulfonyloxy, phenylcarbonyl and phenylcarbonyloxy are preferably unsubstituted or carry one to three halogen atoms and/or one nitro group, one cyano group, one or two methyl, trifluoromethyl, methoxy or trifluoromethoxy groups.

In the formula I, $R^1$ is preferably $C_1$–$C_6$-alkyl, $C_1$–$C_6$-haloalkyl, $C_1$–$C_6$-alkoxy; in particular $C_1$–$C_6$-alkyl; particularly preferably $C_1$–$C_4$-alkyl, most preferably methyl;

$R^2$ is preferably $C_1$–$C_6$-haloalkyl, $C_1$–$C_6$-alkylsulfonyl, halogen or nitro; in particular $C_1$–$C_6$-haloalkyl, preferably difluoromethyl or trifluoromethyl, $C_1$–$C_6$-alkylsulfonyl, or halogen, preferably fluorine or chlorine; particularly preferably $C_1$–$C_4$-alkylsulfonyl, most preferably methylsulfonyl and ethylsulfonyl;

$R^3$ is preferably hydrogen, $C_1$–$C_4$-alkyl or halogen; in particular hydrogen, methyl or chlorine; particularly preferably hydrogen;

$R^4$ is preferably $C_1$–$C_2$-haloalkyl; in particular fluoromethyl, chloromethyl, bromomethyl, difluoromethyl, trifluoromethyl, 1-chloro-1-ethyl, 1-fluoro-1-ethyl or pentafluoroethyl;

$R^5$ is preferably hydrogen, $C_1$–$C_2$-alkyl or $C_1$–$C_2$-haloalkyl; in particular hydrogen, methyl, chloromethyl or trifluoromethyl; particularly preferably hydrogen, methyl or chloromethyl;

$R^6$ is preferably hydrogen or $C_1$–$C_4$-alkyl; in particular hydrogen or methyl;

$R^7$ is preferably hydrogen or $C_1$–$C_4$-alkyl; in particular hydrogen or methyl;

$R^8$ is preferably hydrogen or $C_1$–$C_4$-alkyl; in particular hydrogen or methyl; is preferably hydroxyl, $C_1$–$C_6$-alkoxy, $C_1$–$C_6$-alkylsulfonyloxy, $C_1$–$C_6$-alkylcarbonyloxy, phenyl-$C_1$–$C_2$-alkoxy, phenylcarbonyl-$C_1$–$C_2$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;
  in particular hydroxyl, phenyl-$C_1$–$C_2$-alkoxy, phenylcarbonyl-$C_1$–$C_2$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;
  particularly preferably hydroxyl;

$R^9$ is preferably methyl or ethyl;

$R^{10}$ is preferably hydrogen or $C_1$–$C_4$-alkyl;
  in particular hydrogen, methyl or ethyl;
  particularly preferably hydrogen or methyl.

Particular preference is given to the 3-(4,5-dihydroisoxazol-3-yl)-substituted benzoylpyrazoles of the formula I where $R^4$ is fluoromethyl, chloromethyl, bromomethyl, difluoromethyl, trifluoromethyl, 1-chloro-1-ethyl, 1-fluoro-1-ethyl or pentafluoroethyl;
  is in particular fluoromethyl, chloromethyl, bromomethyl, difluoromethyl or trifluoromethyl.

Extraordinary preference is given to the 3-(4,5-dihydroisoxazol-3-yl)-substituted benzoylpyrazoles of the formula I where $R^1$ is $C_1$–$C_4$-alkyl;

$R^2$ is $C_1$–$C_6$-haloalkyl, $C_1$–$C_6$-alkylsulfonyl, halogen or nitro; and $R^3$ is hydrogen.

Extraordinary preference is likewise given to the 3-(4,5-dihydroisoxazol-3-yl)-substituted benzoylpyrazoles of the formula I where $R^8$ is hydroxyl, phenyl-$C_1$–$C_2$-alkoxy, phenylcarbonyl-$C_1$–$C_2$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

Extraordinary preference is given to the compounds of the formula Ia1 ($\equiv$I where $R^3$=H; $R^8$=OH; $R^9$=$CH_3$ and $R^{10}$=H), in particular to the compounds Ia1.1 to Ia1.72 of Table 1, where the definitions of the radicals $R^1$ to $R^{10}$ are of particular importance for the compounds according to the invention not only in combination with one another, but in each case also on their own.

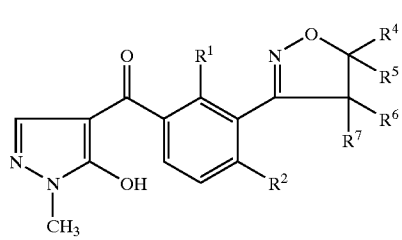

Ia1

TABLE 1

| No. | $R^1$ | $R^2$ | $R^4$ | $R^5$ | $R^6$ | $R^7$ |
|---|---|---|---|---|---|---|
| Ia1.1 | $CH_3$ | $SO_2CH_3$ | $CH_2F$ | H | H | H |
| Ia1.2 | $CH_3$ | $SO_2CH_3$ | $CH_2F$ | $CH_2F$ | H | H |
| Ia1.3 | $CH_3$ | $SO_2CH_3$ | $CH_2F$ | $CH_3$ | H | H |
| Ia1.4 | $CH_3$ | $SO_2CH_3$ | $CH_2Cl$ | H | H | H |
| Ia1.5 | $CH_3$ | $SO_2CH_3$ | $CH_2Cl$ | $CH_2Cl$ | H | H |
| Ia1.6 | $CH_3$ | $SO_2CH_3$ | $CH_2Cl$ | $CH_3$ | H | H |
| Ia1.7 | $CH_3$ | $SO_2CH_3$ | $CH_2Br$ | H | H | H |

TABLE 1-continued

| No. | R¹ | R² | R⁴ | R⁵ | R⁶ | R⁷ |
|---|---|---|---|---|---|---|
| Ia1.8 | CH₃ | SO₂CH₃ | CH₂Br | CH₃ | H | H |
| Ia1.9 | CH₃ | SO₂CH₃ | CHF₂ | H | H | H |
| Ia1.10 | CH₃ | SO₂CH₃ | CHF₂ | CH₃ | H | H |
| Ia1.11 | CH₃ | SO₂CH₃ | CHF₂ | CHF₂ | H | H |
| Ia1.12 | CH₃ | SO₂CH₃ | CF₃ | H | H | H |
| Ia1.13 | CH₃ | SO₂CH₃ | CF₃ | CF₃ | H | H |
| Ia1.14 | CH₃ | SO₂CH₃ | CF₃ | CH₃ | H | H |
| Ia1.15 | CH₃ | SO₂CH₃ | CHClCH₃ | H | H | H |
| Ia1.16 | CH₃ | SO₂CH₃ | CHBrCH₃ | H | H | H |
| Ia1.17 | CH₃ | SO₂CH₃ | CHFCH₃ | H | H | H |
| Ia1.18 | CH₃ | SO₂CH₃ | CF₂CF₃ | H | H | H |
| Ia1.19 | CH₃ | CF₃ | CH₂F | H | H | H |
| Ia1.20 | CH₃ | CF₃ | CH₂F | CH₂F | H | H |
| Ia1.21 | CH₃ | CF₃ | CH₂F | CH₃ | H | H |
| Ia1.22 | CH₃ | CF₃ | CH₂Cl | H | H | H |
| Ia1.23 | CH₃ | CF₃ | CH₂Cl | CH₂Cl | H | H |
| Ia1.24 | CH₃ | CF₃ | CH₂Cl | CH₃ | H | H |
| Ia1.25 | CH₃ | CF₃ | CH₂Br | H | H | H |
| Ia1.26 | CH₃ | CF₃ | CH₂Br | CH₃ | H | H |
| Ia1.27 | CH₃ | CF₃ | CHF₂ | H | H | H |
| Ia1.28 | CH₃ | CF₃ | CHF₂ | CH₃ | H | H |
| Ia1.29 | CH₃ | CF₃ | CHF₂ | CHF₂ | H | H |
| Ia1.30 | CH₃ | CF₃ | CF₃ | H | H | H |
| Ia1.31 | CH₃ | CF₃ | CF₃ | CF₃ | H | H |
| Ia1.32 | CH₃ | CF₃ | CF₃ | CH₃ | H | H |
| Ia1.33 | CH₃ | CF₃ | CHClCH₃ | H | H | H |
| Ia1.34 | CH₃ | CF₃ | CHBrCH₃ | H | H | H |
| Ia1.35 | CH₃ | CF₃ | CHFCH₃ | H | H | H |
| Ia1.36 | CH₃ | CF₃ | CF₂CF₃ | H | H | H |
| Ia1.37 | CH₂CH₃ | SO₂CH₃ | CH₂F | H | H | H |
| Ia1.38 | CH₂CH₃ | SO₂CH₃ | CH₂F | CH₂F | H | H |
| Ia1.39 | CH₂CH₃ | SO₂CH₃ | CH₂F | CH₃ | H | H |
| Ia1.40 | CH₂CH₃ | SO₂CH₃ | CH₂Cl | H | H | H |
| Ia1.41 | CH₂CH₃ | SO₂CH₃ | CH₂Cl | CH₂Cl | H | H |
| Ia1.42 | CH₂CH₃ | SO₂CH₃ | CH₂Cl | CH₃ | H | H |
| Ia1.43 | CH₂CH₃ | SO₂CH₃ | CH₂Br | H | H | H |
| Ia1.44 | CH₂CH₃ | SO₂CH₃ | CH₂Br | CH₃ | H | H |
| Ia1.45 | CH₂CH₃ | SO₂CH₃ | CHF₂ | H | H | H |
| Ia1.46 | CH₂CH₃ | SO₂CH₃ | CHF₂ | CH₃ | H | H |
| Ia1.47 | CH₂CH₃ | SO₂CH₃ | CHF₂ | CHF₂ | H | H |
| Ia1.48 | CH₂CH₃ | SO₂CH₃ | CF₃ | H | H | H |
| Ia1.49 | CH₂CH₃ | SO₂CH₃ | CF₃ | CF₃ | H | H |
| Ia1.50 | CH₂CH₃ | SO₂CH₃ | CF₃ | CH₃ | H | H |
| Ia1.51 | CH₂CH₃ | SO₂CH₃ | CHClCH₃ | H | H | H |
| Ia1.52 | CH₂CH₃ | SO₂CH₃ | CHBrCH₃ | H | H | H |
| Ia1.53 | CH₂CH₃ | SO₂CH₃ | CHFCH₃ | H | H | H |
| Ia1.54 | CH₂CH₃ | SO₂CH₃ | CF₂CF₃ | H | H | H |
| Ia1.55 | CH₃ | SO₂CH₂CH₃ | CH₂F | H | H | H |
| Ia1.56 | CH₃ | SO₂CH₂CH₃ | CH₂F | CH₂F | H | H |
| Ia1.57 | CH₃ | SO₂CH₂CH₃ | CH₂F | CH₃ | H | H |
| Ia1.58 | CH₃ | SO₂CH₂CH₃ | CH₂Cl | H | H | H |
| Ia1.59 | CH₃ | SO₂CH₂CH₃ | CH₂Cl | CH₂Cl | H | H |
| Ia1.60 | CH₃ | SO₂CH₂CH₃ | CH₂Cl | CH₃ | H | H |
| Ia1.61 | CH₃ | SO₂CH₂CH₃ | CH₂Br | H | H | H |
| Ia1.62 | CH₃ | SO₂CH₂CH₃ | CH₂Br | CH₃ | H | H |
| Ia1.63 | CH₃ | SO₂CH₂CH₃ | CHF₂ | H | H | H |
| Ia1.64 | CH₃ | SO₂CH₂CH₃ | CHF₂ | CH₃ | H | H |
| Ia1.65 | CH₃ | SO₂CH₂CH₃ | CHF₂ | CHF₂ | H | H |
| Ia1.66 | CH₃ | SO₂CH₂CH₃ | CF₃ | H | H | H |
| Ia1.67 | CH₃ | SO₂CH₂CH₃ | CF₃ | CF₃ | H | H |
| Ia1.68 | CH₃ | SO₂CH₂CH₃ | CF₃ | CH₃ | H | H |
| Ia1.69 | CH₃ | SO₂CH₂CH₃ | CHClCH₃ | H | H | H |
| Ia1.70 | CH₃ | SO₂CH₂CH₃ | CHBrCH₃ | H | H | H |
| Ia1.71 | CH₃ | SO₂CH₂CH₃ | CHFCH₃ | H | H | H |
| Ia1.72 | CH₃ | SO₂CH₂CH₃ | CF₂CF₃ | H | H | H |

Extraordinary preference is also given to the compounds of the formula Ia2, in particular the compounds Ia2.1 to Ia2.72 which differ from the corresponding compounds Ia1.1 to Ia1.72 in that $R^9$ is ethyl.

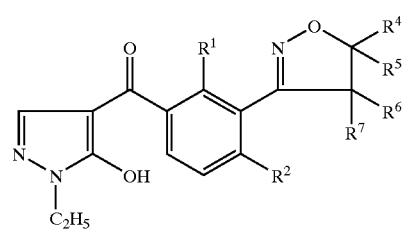

Ia2

Extraordinary preference is also given to the compounds of the formula Ia3, in particular the compounds Ia3.1 to Ia3.72 which differ from the compounds Ia1.1 to Ia1.72 in that $R^{10}$ is methyl.

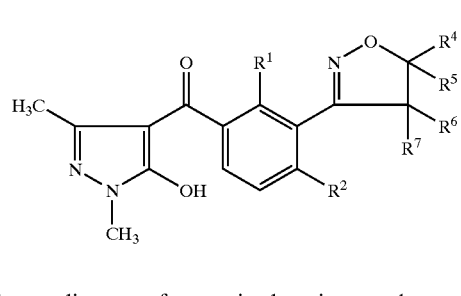

Ia3

Extraordinary preference is also given to the compounds of the formula Ia4, in particular the compounds Ia4.1 to Ia4.72 which differ from the compounds Ia1.1 to Ia1.72 in that $R^9$ is ethyl and $R^{10}$ is methyl.

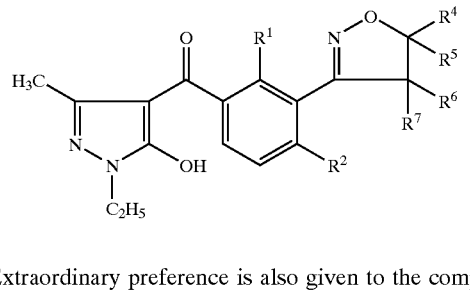

Ia4

Extraordinary preference is also given to the compounds of the formula Ia5, in particular the compounds Ia5.1 to Ia5.72 which differ from the compounds Ia1.1 to Ia1.72 in that $R^8$ is phenylcarbonyloxy.

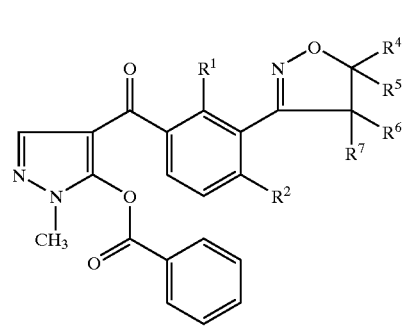

Ia5

Extraordinary preference is also given to the compounds of the formula Ia6, in particular the compounds Ia6.1 to Ia6.72 which differ from the compounds Ia1.1 to Ia1.72 in that $R^8$ is phenylcarbonyloxy and $R^9$ is ethyl.

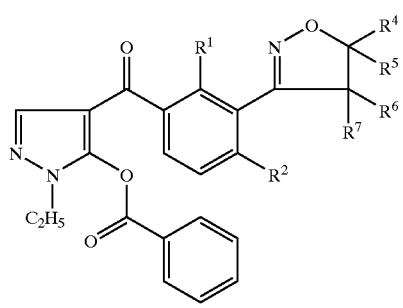

Ia6

Extraordinary preference is also given to the compounds of the formula Ia7, in particular the compounds Ia7.1 to Ia7.72 which differ from the compounds Ia1.1 to Ia1.72 in that $R^8$ is phenylcarbonyloxy and $R^{10}$ is methyl.

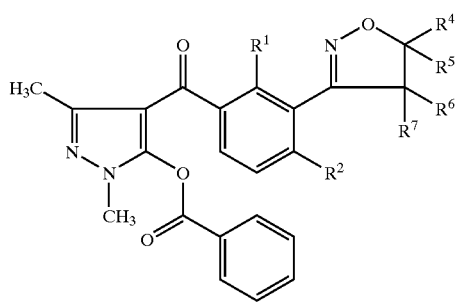

Ia7

Extraordinary preference is also given to the compounds of the formula Ia8, in particular the compounds Ia8.1 to Ia8.72 which differ from the compounds Ia1.1 to Ia1.72 in that $R^8$ is phenylcarbonyloxy, $R^9$ is ethyl and $R^{10}$ is methyl.

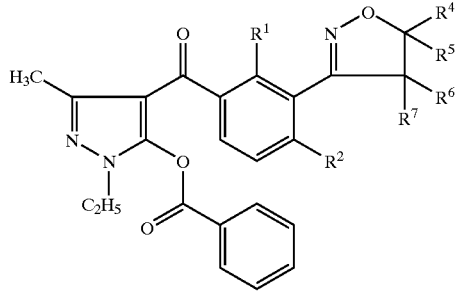

Ia8

Extraordinary preference is also given to the compounds of the formula Ia9, in particular the compounds Ia9.1 to Ia9.72 which differ from the compounds Ia1.1 to Ia1.72 in that $R^8$ is 3-fluorophenylcarbonyloxy.

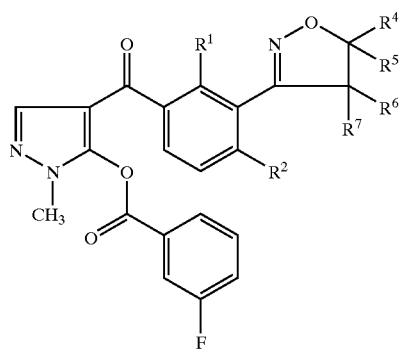

Ia9

Extraordinary preference is also given to the compounds of the formula Ia10, in particular the compounds Ia10.1 to Ia10.72 which differ from the compounds Ia1.1 to Ia1.72 in that RB is 3-fluorophenylcarbonyloxy and $R^9$ is ethyl.

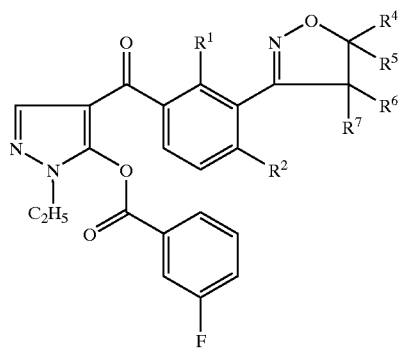

Ia10

Extraordinary preference is also given to the compounds of the forrmula Ia11, in particular the compounds Ia11.1 to Ia11.72 which differ from the compounds Ia1.1 to Ia1.72 in that $R^8$ is 3-trifluoromethylphenylcarbonyloxy.

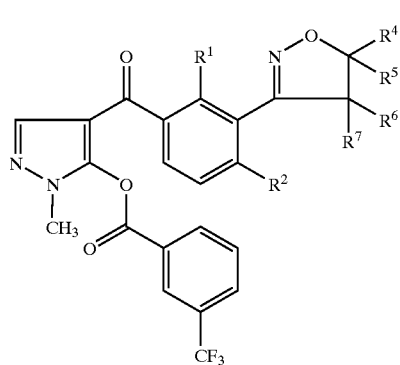

Ia11

Extraordinary preference is also given to the compounds of the formula Ia12, in particular the compounds Ia12.1 to Ia12.72 which differ from the compounds Ia1.1 to Ia1.72 in that $R^8$ is 3-trifluorophenylcarbonyloxy and $R^9$ is ethyl.

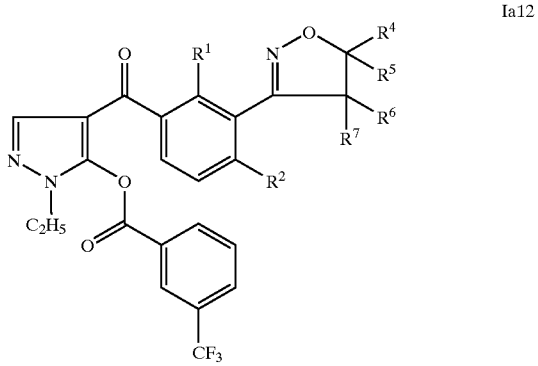

Extraordinary preference is also given to the compounds of the formula Ia13, in particular the compounds Ia13.1 to Ia13.72 which differ from the compounds Ia1.1 to Ia1.72 in that $R^8$ is 3-chlorophenylcarbonyloxy.

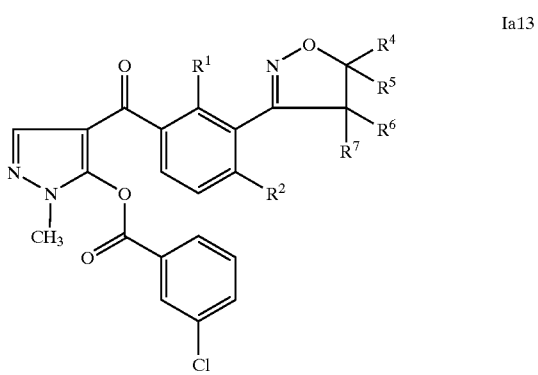

Extraordinary preference is also given to the compounds of the formula Ia14, in particular the compounds Ia14.1 to Ia14.72 which differ from the compounds Ia1.1 to Ia1.72 in that $R^8$ is 3-chlorophenylcarbonyloxy and $R^9$ is ethyl.

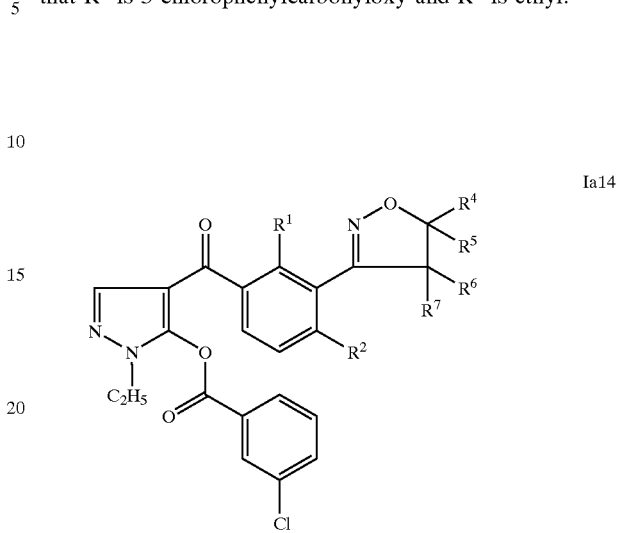

The 3-(4,5-dihydroisoxazol-3-yl)-substituted benzoylpyrazoles of the formula I can be obtained by various routes, for example by the processes below.

Reaction of pyrazoles of the formula II with an activated benzoic acid derivative IIIα or a benzoic acid IIIβ, which is preferably activated in situ, to give the corresponding acylation product I' and subsequent rearrangement affords compounds of the formula I where $R^8$=OH.

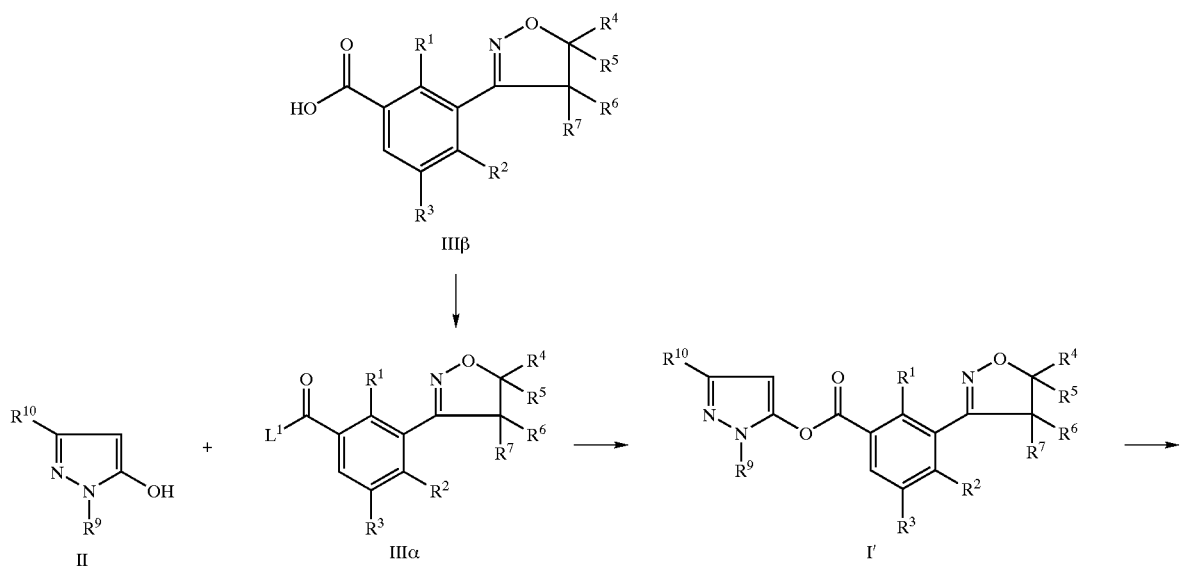

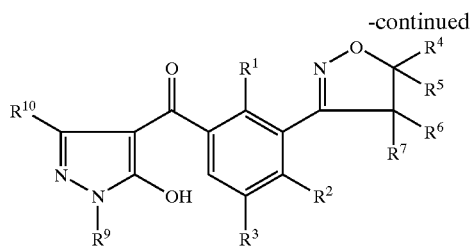

I where R⁸ = OH $L^1$ is a nucleophilically displaceable leaving group, such as halogen, for example bromine or chlorine, hetaryl, for example imidazolyl or pyridyl, carboxylate, for example acetate, trifluoroacetate, etc.

The activated benzoic acid can be employed directly, such as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. The reactants and the auxiliary base are advantageously employed in this case in equimolar amounts. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate, or mixtures of these.

If the activated carboxylic acid component used is a benzoyl halide, it may be advantageous to cool the reaction mixture to 0–10° C. when adding this reaction partner. The mixture is subsequently stirred at 20–100° C., preferably at 25–50° C., until the reaction has ended. Work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester I' can be employed for the rearrangement without any further purification.

The rearrangement of the esters I' to the compounds of the formula I is advantageously carried out at 20–40° C. in a solvent and in the presence of a base and, if appropriate, using a cyano compound as catalyst.

Suitable solvents are, for example, acetonitrile, methylene chloride, 1,2-dichloroethane, dioxane, ethyl acetate, dimethoxyethane, tetrahydrofuran, toluene or mixtures of these. Preferred solvents are acetonitrile and dioxane.

Suitable bases are tertiary amines, such as triethylamine or pyridine or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated. (Examples for the preparation of esters of hydroxypyrazoles and for the rearrangement of the esters are given, for example, in EP-A 282 944 and U.S. Pat No. 4,643,757).

However, it is also possible to generate the "acylation product" I' in situ by reacting a pyrazole of the formula II, or an alkali metal salt thereof with a 3-(4,5-dihydroisoxazol-3-yl)benzene derivative of the formula IV in the presence of carbon monoxide, a catalyst and a base.

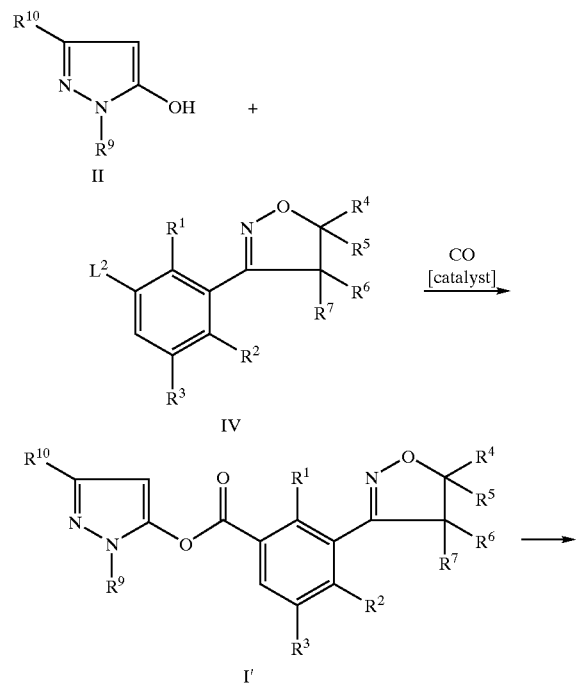

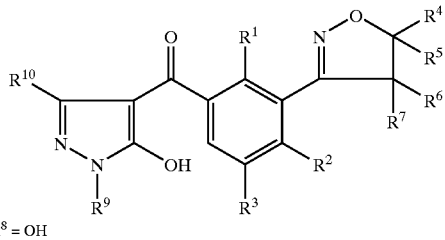

I where $R^8$ = OH $L^2$ is a leaving group, such as halogen, for example chlorine, bromine or iodine, or sulfonate, such as mesylate or triflate; preference is given to bromine or triflate.

The "acylation product" I' proceeds to react under the reaction conditions, generally directly, to give the 3-(4,5-dihydroisoxazol-3-yl)-substituted benzoylpyrazole of the formula I.

Suitable catalysts are palladium-ligand complexes in which the palladium is present in oxidation state 0, metallic palladium, which has optionally been absorbed on a carrier, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert carrier such as, for example, activated carbon, silica, alumina, barium sulfate or calcium carbonate. The reaction is preferably carried out in the presence of complex ligands such as, for example, triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction is preferably carried out with metallic palladium or palladium(II) salts, are tertiary phosphines whose structure is represented by the following formulae:

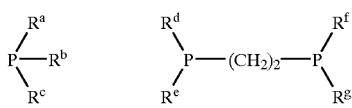

where z is 1 to 4 and the radicals $R^a$ to $R^g$ are $C_1$–$C_6$-alkyl, $C_3$–$C_6$-cycloalkyl, aryl-$C_1$–$C_2$-alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines such as, for example, triphenylphosphine, tricyclohexylphosphine, or 1,2-bis(diphenylphosphino)ethane. Many of the complexed palladium salts are also commercially available. Preferred palladium salts are [(R)(+)2,2'-bis(diphenylphosphino)-1,1'-binaphthyl]palladium(II) chloride, bis(triphenylphosphine)palladium(II) acetate and, in particular, bis(triphenylphosphine)palladium(II) chloride.

The palladium catalyst is usually employed in a concentration of from 0.05 to 5 mol%, and preferably 1–3 mol%.

Suitable bases are tertiary amines, such as, for example, N-methylpiperidine, ethyldiisopropylamine, 1,8-bisdimethylaminonaphthalene or, in particular, triethylamine. Also suitable is alkali metal carbonate, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the 3-(4,5-dihydroisoxazo-3-yl)benzene derivative of the formula IV.

Suitable solvents are nitriles, such as benzonitrile and acetonitrile, aromatic hydrocarbons, such as toluene, amides, such as dimethylformamide, dimethylacetamide, tetra-$C_1$–$C_4$-alkylureas or N-methylpyrrolidone and, preferably, ethers, such as tetrahydrofuran and methyl tert-butyl ethers. Particular preference is given to ethers, such as 1,4-dioxane and dimethoxyethane.

Compounds of the formula I where $R^8 \neq$ hydroxyl are obtained by reacting compounds of the formula I where $R^8$=hydroxyl with alkylating agents, sulfonylating agents or acylating agents $L^3$-$R^{8a}$ (V)

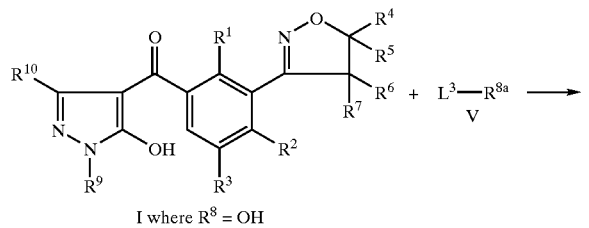

I where $R^8$ = OH

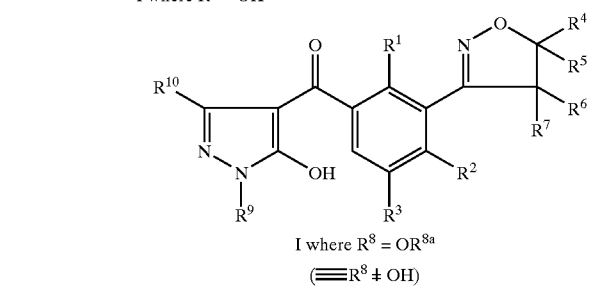

I where $R^8$ = $OR^{8a}$ ($\equiv R^8 \neq OH$)

$L^3$ is a nucleophilically displaceable leaving group, such as halogen, for example bromine or chlorine, acyloxy, for example acetyloxy or ethylcarbonyloxy, or alkylsulfonyloxy, for example methylsulfonyloxy or trifluoromethylsulfonyloxy.

$R^{8a}$ is $C_1$–$C_6$-alkyl, $C_3$–$C_6$-alkenyl, $C_1$–$C_6$-alkylsulfonyl, $C_1$–$C_6$-alkylcarbonyl, phenyl-$C_1$–$C_4$-alkyl, phenylcarbonyl-$C_1$–$C_4$-alkyl, phenylsulfonyl or phenylcarbonyl, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

The compounds of the formula V can be employed directly, such as, for example, in the case of the sulfonyl halides or sulfonic anhydrides, or be generated in situ, for example activated sulfonic acids (using sulfonic acid and dicyclohexylcarbonyldiimide, carbonyldiimidazole, etc.).

The starting materials are generally employed in equimolar amounts. However, it may also be advantageous to employ an excess of one or the other component.

If appropriate, it may be advantageous to carry out the reaction in the presence of a base. The reactants and the auxiliary base are advantageously employed in equimolar amounts. An excess of auxiliary base, for example from 1.5 to 3 molar equivalents, based on I (where $R^8$=OH), may be advantageous in certain cases.

Suitable auxiliary bases are tertiary alkylamines, such as triethylamine, pyridine, alkali metal carbonates, for example sodium carbonate or potassium carbonate, and alkali metal hydrides, for example sodium hydride. Preference is given to using triethylamine and pyridine.

Suitable solvents are, for example, chlorinated hydrocarbons, such as methylene chloride and 1,2-dichloroethane, aromatic hydrocarbons, for example toluene, xylene, chlorobenzene, ethers, such as diethyl ether, methyl tert-butyl ether, tetrahydrofuran and dioxane, polar aprotic solvents, such as acetonitrile, dimethylformamide, dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

The pyrazoles of the formula II used as starting materials are known or can be prepared by processes known per se (for example EP-A 240 001 and J. Prakt. Chem. 315, 383 (1973)).

The compounds of the formulae III and IV

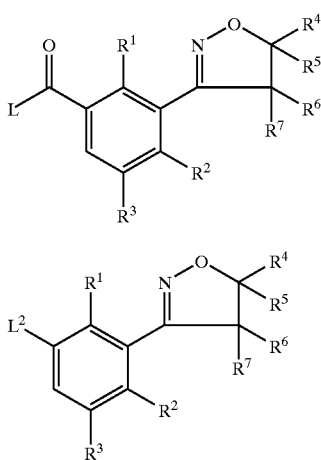

where in each case the variables $R^1$ to $R^7$ are as defined for the compounds of the formula I and L is hydroxyl or a radical which can be removed by hydrolysis; or $L^2$ is a nucleophilically displaceable leaving group, are both as such novel.

Examples of radicals which can be removed by hydrolysis are alkoxy, phenoxy, alkylthio and phenylthio radicals, which may be substituted, halides and hetaryl radicals attached via nitrogen, amino and imino radicals, which may be substituted, etc.

Examples of nucleophilically displaceable leaving groups are halogen, $C_1$–$C_4$-alkylsulfonyl and $C_1$–$C_4$-haloalkylsulfonyloxy.

Preferred compounds of the formula III are those in which L is halogen, in particular chlorine or bromine.

Also preferred are those compounds of the formula III in which L is $C_1$–$C_6$-alkoxy.

Preference is likewise given to those compounds of the formula III in which L is hydroxyl.

With respect to the variables $R^1$ to $R^7$, the particularly preferred embodiments of the compounds of the formula III or IV correspond to those of the 3-(4,5-dihydroisoxazol-3-yl)-substituted benzoylpyrazoles of the formula I.

The compounds of the formula III or IV can be prepared similarly to known processes (cf. WO 96/26206, WO 98/31681 and PCT/EP99/03006). Thus, the compounds of the formula IIIβ (=III where L=hydroxyl) or the 3-(4,5-dihydroisoxazol-3-yl)benzene derivatives IV can be converted into 4,5-dihydroisoxazol-3-yl derivatives III or IV by conversion of oximes of the formula VI or VII in a manner known per se via the hydroxamic acid halide intermediate, in particular via the hydroxamic acid chlorides. The latter are employed to generate nitrile oxides in situ which are reacted with alkenes to give the desired products (cf, for example, Chem. Ber. 106, 3258–3274 (1972)).

The compounds of the formula III (where L=$C_1$–$C_6$-alkoxy) are then converted in a manner known per se by hydrolysis into the benzoic acid IIIβ.

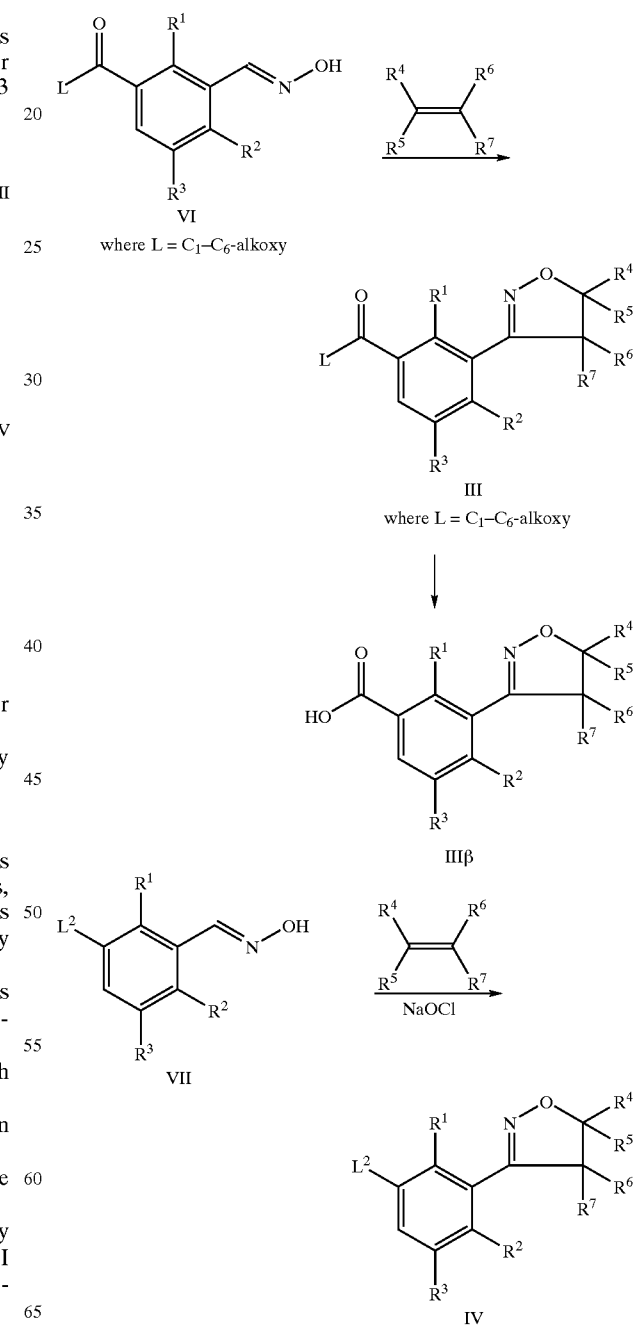

PREPARATION EXAMPLES

Synthesis of the End Products

Example 1

4-[2-Methyl-3-(5-chloromethyl-4,5-dihydroisoxazol-3-yl)-4-methyl-sulfonylbenzoyl]-5-hydroxy-1-methyl-1H-pyrazole (Compound 2.1)

Step a)

With ice-cooling, 0.70 g (1.99 mmol) of 2-methyl-3-(5-chloromethyl-4,5-dihydroisoxazol-3-yl)-4-methyl-sulfonylbenzoyl chloride in 40 ml of tetrahydrofuran was added dropwise to a mixture of 0.2 g (1.99 mmol) of 1-methyl-5-hydroxy-1H-pyrazole, 0.40 g (4 mmol) of triethylamine and 40 ml of tetrahydrofuran. After 12 hours of stirring at room temperature, the solvent was removed and the residue was taken up in ethyl acetate and washed with aqueous potassium carbonate solution and water. The solution was then dried and the solvent was distilled off. This gave 0.82 g of an amorphous foam which was used for further reactions without further purification.

Step b)

A mixture of 0.82 g of the product from step a) and 0.41 g (2.99 mmol) of potassium carbonate in 5 ml of dioxane was refluxed for five hours. After cooling and removal of the solvent, the residue was taken up in water and washed with diethyl ether. The aqueous phase was adjusted to pH 1–2 using hydrochloric acid and extracted with methylene chloride. These combined organic phases were washed with water and dried, and the solvent was distilled off. This gave 0.69 g (84% of theory) of an amorphous powder. The $^1$H-NMR spectrum found corresponded to the given structure of the title compound.

Synthesis of the Intermediates

Example 2

2-Methyl-3-[5-(4-chlorobutyl)-4,5-dihydroisoxazol-3-yl]-4-methyl-sulfonylbenzoic Acid Step a):

1-Bromo-2-methyl-3-[5-(4-chlorobutyl)-4,5-dihydroisoxazol-3-yl]-4-methylsulfonylbenzene (Compound 4.1)

At room temperature, 50 ml of sodium hypochlorite solution (12.5% of active chlorine, admixed with a spatula tip of sodium acetate) were added dropwise with vigorous stirring to a solution of 15 g (51.4 mmol) of 3-bromo-2-methyl-6-methylsulfonylbenzaldehyde oxime and 6.7 g (56.5 mmol) of 6-chlorohexene in 200 ml of methylene chloride. The reaction mixture was stirred at room temperature overnight. The reaction mixture was then stirred into 300 ml of water. The organic phase was washed three times with water, dried and concentrated to dryness. This gave 19.3 g of a viscous yellow oil (92.4% of theory). The $^1$H-NMR spectrum corresponds to the given structure.

Step b):

2-Methyl-3-[5-(4-chlorobutyl)-4,5-dihydroisoxazol-3-yl]-4-methyl-sulfonylbenzoic Acid (Compound 3.2)

14.5 g (35.5 mmol) of the compound obtained in step a), 0.4 g of palladium acetate (0.05 equivalents), 2 g of tricyclohexylphosphine (0.2 equivalents), 1.5 g of lithium chloride (1 equivalent), 7.2 g of triethylamine (2 equivalents), 100 ml of toluene and 50 ml of water were filled into a miniature autoclave. The reaction mixture was stirred at 140° C. under a carbon monoxide pressure of 20 bar for 12 hours. After cooling, the reaction mixture was discharged using water. The phases were separated, and the organic phase was extracted once with 5% strength aqueous sodium hydroxide. The combined aqueous phases were washed twice with diethyl ether, dried and evaporated to dryness. This gave 3.2 g of a viscous yellow oil (24.1% of theory). The $^1$H-NMR spectrum found corresponds to the given structure.

Example 3

2-Methyl-3-[5,5-bis(chloromethyl)-4,5-dihydroisoxazol-3-yl]-4-methylsulfonylbenzoyl Chloride (Compound 3.4)

Step a):

1-Bromo-2-methyl-3-[5,5-di(chloromethyl)-4,5-dihydroisoxazol-3-yl]-4-methylsulfonylbenzene (Compound 4.2)

At room temperature, 50 ml of sodium hypochlorite solution (which contained 3.8 g (51.4 mmol) of NaOCl, admixed with a spatula tip of sodium acetate) were added dropwise with stirring to a solution of 15 g (51.4 mmol) of 3-bromo-2-methyl-6-methylsulfonylbenzaldehyde oxime and 7.1 g (56.5 mmol) of 2-chloromethyl-3-chloropropene in 250 ml of methylene chloride. The reaction mixture was stirred at room temperature overnight. The phases were separated, and the organic phase was washed three times with water, dried and evaporated to dryness. The residue was chromatographed on silica gel using, as mobile phase, first cyclohexane, then cyclohexane/ethyl acetate 90:10 and finally cyclohexane/ethyl acetate 80:20. This gave 13.5 g of a white powder (63.3% of theory). M.p.: 144–145° C. The $^1$H-NMR spectrum found corresponds to the given structure.

Step b):

2-Methyl-3-[5,5-bis(chloromethyl)-4,5-dihydroisoxazol-3-yl]-4-methylsulfonylbenzoic Acid (Compound 3.3)

12 g (28.91 mmol) of the compound obtained in step a), 0.32 g (0.05 equivalents) of palladium acetate, 1.6 g (0.2 equivalents) of tricyclohexylphosphine, 1.23 g (1 equivalent) of lithium chloride, 5.84 g (2 equivalents) of triethylamine, 100 ml of toluene and 50 ml of water were filled into an autoclave. The autoclave was flushed six times with carbon monoxide. The reaction mixture was then stirred at 140° C. under a carbon monoxide pressure of 20 bar for 12 hours. After cooling, the reaction mixture was discharged using water. The phases were separated and the organic phase was extracted twice using 5% strength NaOH. The combined aqueous phases were washed with diethyl ether, the pH of the aqueous phase was adjusted to 1–2 and the aqueous phase was extracted three times with methylene chloride. The organic phase was washed twice with water, dried and concentrated to dryness. This gave 9.6 g of a white powder (87.4% of theory). The $^1$H-NMR spectrum found corresponds to the given structure.

Step c):

2-Methyl-3-[5,5-bis(chloromethyl)-4,5-dihydroisoxazol-3-yl]-4-methylsulfonylbenzoyl Chloride (Compound 3.4)

At room temperature, 5.4 g (45.26 mmol) of thionyl chloride were added dropwise to a solution of 8.6 g (22.63 mmol) of the compound obtained in step b) in a mixture of 150 ml of toluene and 3 drops of dimethylformamide. The reaction mixture was stirred at room temperature for 6 hours and then evaporated to dryness. Three times, the residue was taken up in methylene chloride and evaporated to dryness. This gave 9.0 g of a viscous brown oil (100% of theory).

Example 4

1-Bromo-2-methyl-3-[5-bromomethyl-4,5-dihydroisoxazol-3-yl]-4-methylsulfonylbenzene At 55–60° C., 2.33 g (17.1 mmol) of N-chlorosuccinimide were added in portions to a solution of 5.0 g (17.1 mmol) of 3-bromo-2-methyl-6-methylsulfonylbenzaldehyde oxime in 200 ml of dimethylformamide. After 30 minutes of stirring, the reaction mixture was cooled and introduced into ice-water, and the residue was filtered off, washed with water and dried. The resulting product was suspended in methylene chloride, and 1.7 g (17.1 mmol) of triethylamine and then 2.48 g (20.1 mmol) of alkyl bromide were added dropwise. The reaction mixture was stirred at room temperature for 12 hours and then washed with water and dried, and the solvent was removed. This gave 5.91 g of a pale solid. The $^1$H-NMR spectrum found corresponded to the given structure of the title compound.

In addition to the compounds above, Tables 2 to 4 list further compounds of the formulae I, III and IV which were prepared or are preparable in a similar manner.

TABLE 2

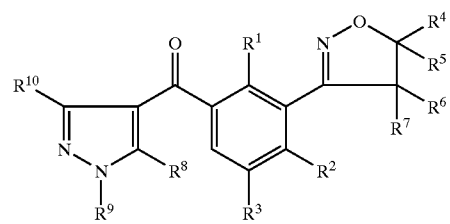

I

| No. | $R^1$ | $R^2$ | $R^3$ | $R^4$ | $R^5$ | $R^6$ | $R^7$ | $R^8$ | $R^9$ | $R^{10}$ | physical data m.p. [° C.] |
|---|---|---|---|---|---|---|---|---|---|---|---|
| 2.1 | $CH_3$ | $CH_3SO_2$ | H | $CH_2Cl$ | H | H | H | OH | $CH_3$ | H | 76–78 |
| 2.2 | $CH_3$ | $CH_3SO_2$ | H | $CH_2Cl$ | H | H | H | OH | $CH_2CH_3$ | H | 73–77 |
| 2.3 | $CH_3$ | $CH_3SO_2$ | H | $CH_2Cl$ | H | H | H | OH | $CH_3$ | $CH_3$ | 74–77 |
| 2.4 | $CH_3$ | $CH_3SO_2$ | H | $CH_2Cl$ | $CH_2Cl$ | H | H | OH | $CH_3$ | H | 76–80 |
| 2.5 | $CH_3$ | $CH_3SO_2$ | H | $CH_2Cl$ | $CH_2Cl$ | H | H | OH | $CH_2CH_3$ | H | 74–80 |
| 2.6 | $CH_3$ | $CH_3SO_2$ | H | $CH_2Cl$ | $CH_2Cl$ | H | H | OH | $CH_3$ | $CH_3$ | 81–86 |
| 2.7[1)] | $CH_3$ | $CH_3SO_2$ | H | $CH_2Cl$ | H | $CH_3$ | H | OH | $CH_3$ | H | 85–100 |
| 2.8 | $CH_3$ | $CH_3SO_2$ | H | $CH_2Cl$ | H | $CH_3$ | H | OH | $CH_2CH_3$ | H | |
| 2.9 | $CH_3$ | $CH_3SO_2$ | H | $CH_2Cl$ | H | $CH_3$ | H | OH | $CH_3$ | $CH_3$ | |
| 2.10 | $CH_3$ | $CH_3SO_2$ | H | $CH_2Cl$ | $CH_3$ | H | H | OH | $CH_3$ | H | 105–110 |
| 2.11[2)] | $CH_3$ | $CH_3SO_2$ | H | $CH_2Cl$ | H | $CH_3$ | H | OH | $CH_3$ | H | 85–95 |
| 2.12 | $CH_3$ | $CH_3SO_2$ | H | $CHF_2$ | H | H | H | OH | $CH_3$ | H | 73–76 |
| 2.13 | $CH_3$ | $CH_3SO_2$ | H | $CHF_2$ | H | H | H | OH | $CH_2CH_3$ | H | 71–75 |

[1)]trans-isomer
[2)]cis-isomer

TABLE 3

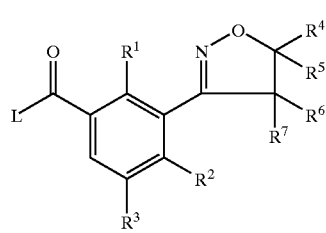

III

| No. | $R^1$ | $R^2$ | $R^3$ | $R^4$ | $R^5$ | $R^6$ | $R^7$ | L | physical data m.p. [° C.] |
|---|---|---|---|---|---|---|---|---|---|
| 3.1 | $CH_3$ | $CH_3SO_2$ | H | $CH_2Cl$ | H | H | H | Cl | oil |
| 3.2 | $CH_3$ | $CH_3SO_2$ | H | $(CH_2)_4Cl$ | H | H | H | OH | oil |
| 3.3 | $CH_3$ | $CH_3SO_2$ | H | $CH_2Cl$ | $CH_2Cl$ | H | H | OH | |
| 3.4 | $CH_3$ | $CH_3SO_2$ | H | $CH_2Cl$ | $CH_2Cl$ | H | H | Cl | oil |
| 3.5 | $CH_3$ | $CH_3SO_2$ | H | $CH_2Cl$ | H | H | H | OH | 43–48 |

TABLE 4

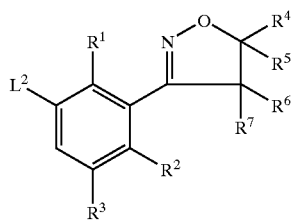

IV

| No. | R¹ | R² | R³ | R⁴ | R⁵ | R⁶ | R⁷ | L² | physical data m.p. [° C.] |
|---|---|---|---|---|---|---|---|---|---|
| 4.1 | CH₃ | CH₃SO₂ | H | (CH₂)₄Cl | H | H | H | Br | oil |
| 4.2 | CH₃ | CH₃SO₂ | H | CH₂Cl | CH₂Cl | H | H | Br | 144–145 |
| 4.3 | CH₃ | CH₃SO₂ | H | CH₂Br | H | H | H | Br | |
| 4.4 | CH₃ | CH₃SO₂ | H | CH₂Cl | H | H | H | Br | 138–140 |

The 3-(4,5-dihydroisoxazol-3-yl)-substituted benzoylpyrazoles of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I, or the herbicidal compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. altissima, *Beta vulgaris* spec. rapa, *Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N.rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. vulgare), *Theobroma cacao, Trifolium pratense, Triticum aestivum, Triticum durum, Vicia faba, Vitis vinifera* and *Zea mays*.

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should guarantee a very fine distribution of the active compounds according to the invention.

The herbicidal compositions comprise a herbicidally effective amount of at least one compound of the formula I or an agriculturally useful salt of I and auxiliaries which are customary for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 3-(4,5-dihydroisoxazol-3-yl)-substituted benzoylpyrazoles, either as such or dissolved in an oil or solvent, can be homogenized in water by means of a wetting agent, tackifier, dispersant or emulsifier. Alternatively, it is possible to prepare concentrates consisting of active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably from 0.01 to 95% by weight of at least one active compound. The active compounds are employed in a purity of from 90% to 100%, preferably from 95% to 100% (according to the NMR spectrum).

The formulation examples below illustrate the production of such preparations:

I. 20 parts by weight of the compound No. 2.3 are dissolved in a mixture consisting of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.3 are dissolved in a mixture consisting of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.3 are dissolved in a mixture consisting of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 2.3 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.3 are mixed with 97 parts by weight of finely divided kaolin. This gives a dust which comprises 3% by weight of the active compound.

VI. 20 parts by weight of the active compound No. 2.3 are mixed intimately with 2 parts by weight of the calcium salt of dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 2.3 is dissolved in a mixture consisting of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 2.3 is dissolved in a mixture consisting of 80 parts by weight of cyclohexanone and 20 parts by weight of Wettol® EM 31 (nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably from 0.01 to 1.0 kg/ha of active substance (a.s.), depending on the control target, the season, the target plants and the growth stage.

To widen the activity spectrum and to achieve synergistic effects, the 3-(4,5-dihydroisoxazol-3-yl)-substituted benzoylpyrazoles of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the 3-(4,5-dihydroisoxazol-3-yl)-substituted benzoylpyrazoles of the formula I was demonstrated by the following greenhouse experiments:

The cultivation containers used were plastic pots containing loamy sand with approximately 3.0% of humus as the substrate. The seeds of the test plants were sown separately for each species.

For the pre-emergence treatment, directly after sowing, the active compounds, which had been suspended or emulsified in water, were applied by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.25 or 0.125 kg/ha of a.s. (active substance). Depending on the species, the plants were kept at 10–25° C. or 20–35° C. The test period extended over from 2 to 4 weeks. During this time, the plants were tended, and their response to the individual treatments was evaluated.

Evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Common name |
| --- | --- |
| Amaranthus retroflexus | pig weed |
| Brachiaria plantaginea | alexandergrass |
| Chenopodium album | lambsquaters |
| Echinochloa crus galli | barnyardgrass |
| Polygonum persicaria | ladysthumb |
| Setaria faberi | giant foxtail |

At application rates of 0.25 or 0.125 kg/ha, compound 2.3 (Table 2) showed very good post-emergence action against the abovementioned undesirable plants.

We claim:

1. A 3-(4,5-dihydroisoxazol-3-yl)-substituted benzoylpyrazole of the formula I

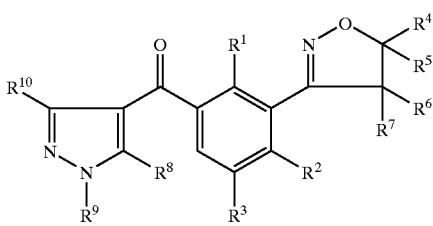

in which
$R^1$ is $C_1$–$C_6$-alkyl, $C_1$–$C_6$-haloalkyl, $C_1$–$C_6$-alkoxy or $C_1$–$C_6$-haloalkoxy;
$R^2$ is $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl, halogen, cyano or nitro;
$R^3$ is hydrogen, $C_1$–$C_6$-alkyl or halogen;
$R^4$ is $C_1$–$C_4$-haloalkyl;
$R^5$, $R^6$, $R^7$ independently of one another are hydrogen, $C_1$–$C_4$-alkyl or $C_1$–$C_4$-haloalkyl;
$R^8$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, phenyl-$C_1$–$C_4$-alkoxy, phenylcarbonyl-$C_1$–$C_4$-alkoxy, phenylsulfonyloxy or phenylcarbonyloxy, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;
$R^9$ is hydrogen or $C_1$–$C_2$-alkyl; and
$R^{10}$ is hydrogen or $C_1$–$C_4$-alkyl;
and its agriculturally useful salts.

2. A 3-(4,5-dihydroisoxazol-3-yl)-substituted benzoylpyrazole as claimed in claim 1, wherein
$R^4$ is fluoromethyl, chloromethyl, bromomethyl, difluoromethyl, trifluoromethyl, 1-chloro-1-ethyl, 1-fluoro-1-ethyl or pentafluoroethyl.

3. A 3-(4,5-dihydroisoxazol-3-yl)-substituted benzoylpyrazole as claimed in claim 1, wherein
$R^1$ is $C_1$–$C_4$-alkyl;
$R^2$ is $C_1$–$C_6$-haloalkyl, $C_1$–$C_8$-alkylsulfonyl, halogen or nitro; and
$R^3$ is hydrogen.

4. A 3-(4,5-dihydroisoxazol-3-yl)-substituted benzoylpyrazole as claimed in claim 1, wherein
$R^8$ is hydroxyl, phenyl-$C_1$–$C_2$-alkoxy, phenylcarbonyl-$C_1$–$C_2$-alkoxy, phenylsulfonyloxy, phenylcarbonyloxy, where the phenyl radical of the four lastmentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

5. A process for preparing 3-(4,5-dihydroisoxazol-3-yl)-substituted benzoylpyrazoles as claimed in claim 1, which comprises acylating a pyrazole of the formula II

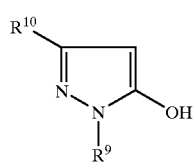

with an activated benzoic acid IIIα or a benzoic acid IIIβ

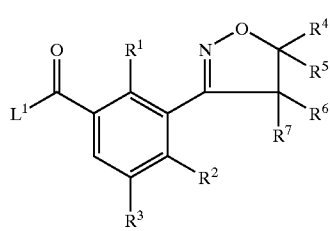

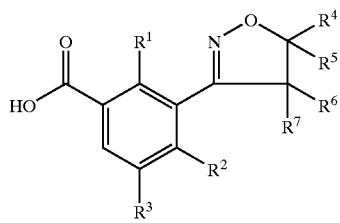

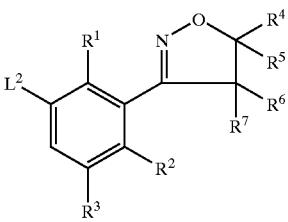

where $R^1$ to $R^7$, $R^9$ and $R^{10}$ are as defined in claim 1 and $L^1$ is a nucleophilically displaceable leaving group; rearranging the acylation product to a compound of the formula I where $R^8$=hydroxyl; and, if appropriate, reacting the product of the rearrangement with a compound of the formula V $$L^3\text{—}R^{8a} \qquad \qquad V$$

where $L^3$ is a nucleophilically displaceable leaving group; and
$R^{8a}$ is $C_1$–$C_6$-alkyl, $C_3$–$C_6$-alkenyl, $C_1$–$C_6$-alkylsulfonyl, $C_1$–$C_6$-alkylcarbonyl, phenyl-$C_1$–$C_4$-alkyl, phenylcarbonyl-$C_1$–$C_4$-alkyl, phenylsulfonyl or phenylcarbonyl, where the phenyl radical of the four lastmentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy.

6. A process for preparing 3-(4,5-dihydroisoxazol-3-yl)-substituted benzoylpyrazoles as claimed in claim 1, which comprises reacting a pyrazole of the formula II

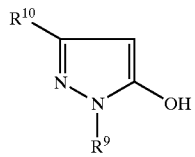

in which $R^9$ and $R^{10}$ are as defined in claim 1, or an alkali metal salt thereof, with a 3-(4,5-dihydroisoxazol-3-yl) benzene derivative of the formula IV where $R^1$ to $R^7$ are as defined in claim 1 and $L^2$ is a leaving group, in the presence of carbon monoxide, a catalyst and a base to give a compound of the formula I where $R^8$=hydroxyl;

and, if appropriate, reacting the reaction product with a compound of the formula V $$L^3\text{—}R^{8a} \qquad \qquad V$$

where $L^3$ and $R^{8a}$ are as defined in claim 5.

7. A composition, comprising a herbicidally effective amount of at least one 3-(4,5-dihydroisoxazol-3-yl)-substituted benzoylpyrazole of the formula I or an agriculturally useful salt of I as claimed in claim 1 and auxiliaries customarily used for formulating crop protection agents.

8. A process for preparing compositions as claimed in claim 7, which comprises mixing a herbicidally effective amount of at least one 3-(4,5-dihydroisoxazol-3-yl)-substituted benzoylpyrazole of the formula I or an agriculturally useful salt of I and auxiliaries customarily used for formulating crop protection agents.

9. A method for controlling undesirable vegetation, which comprises allowing a herbicidally effective amount of at least one 3-(4,5-dihydroisoxazol-3-yl)-substituted benzoylpyrazole of the formula I or an agriculturally useful salt of I as claimed in claim 1 to act on plants, their habitat and/or on seeds.

10. The use of the 3-(4,5-dihydroisoxazol-3-yl)-substituted benzoylpyrazoles of the formula I and/or their agriculturally useful salts as claimed in claim 1 as herbicides.

* * * * *

UNITED STATES PATENT AND TRADEMARK OFFICE
CERTIFICATE OF CORRECTION

PATENT NO.     : 6,613,719 B1
DATED          : September 2, 2003
INVENTOR(S)    : Kudis et al.

It is certified that error appears in the above-identified patent and that said Letters Patent is hereby corrected as shown below:

Column 30,
Line 30, "$C_1$-$C_8$-alkylsulfonyl" should be -- $C_1$-$C_6$-alkylsulfonyl --.

Signed and Sealed this

Twentieth Day of January, 2004

JON W. DUDAS
*Acting Director of the United States Patent and Trademark Office*